(12) United States Patent
Shahinia, Jr.

(10) Patent No.: US 6,350,781 B1
(45) Date of Patent: *Feb. 26, 2002

(54) METHOD AND ANALGESIC PREPARATIONS FOR SUSTAINED AND EXTENDED CORNEAL ANALGESIA WITH SUBANESTHETIC CONCENTRATIONS OF LIDOCAINE

(76) Inventor: Lee Shahinia, Jr., 1506 Country Club Dr., Los Altos, CA (US) 94024

( * ) Notice: Subject to any disclaimer, the term of this patent is extended or adjusted under 35 U.S.C. 154(b) by 0 days.

This patent is subject to a terminal disclaimer.

(21) Appl. No.: 09/648,029

(22) Filed: Aug. 25, 2000

Related U.S. Application Data

(63) Continuation-in-part of application No. 09/442,066, filed on Nov. 16, 1999, now abandoned, which is a continuation of application No. 09/088,594, filed on Jun. 2, 1998, now abandoned, which is a continuation-in-part of application No. 09/816,762, filed on Mar. 11, 1997, now Pat. No. 5,760,077, which is a continuation-in-part of application No. 08/415,184, filed on Apr. 3, 1995, now Pat. No. 5,610,184, which is a continuation-in-part of application No. 08/183,186, filed on Jan. 14, 1994, now abandoned.

(51) Int. Cl.[7] ............................................... A61K 31/24
(52) U.S. Cl. ...................... 514/540; 514/563; 514/912
(58) Field of Search ................................ 514/540, 563, 514/912

(56) References Cited

U.S. PATENT DOCUMENTS 5,411,738 A * 5/1995 Hind ........................... 424/445

* cited by examiner

Primary Examiner—Zohren Fay
(74) Attorney, Agent, or Firm—Hana Verny, Esq.

(57) ABSTRACT

A preparation suitable for sustained and extended corneal analgesia and for repeated administration consisting of subanesthetic concentrations of lidocaine. A method for corneal analgesia by administering to a patient an ophthalmic analgesic solution containing lidocaine in subanesthetic 0.4% concentration.

20 Claims, 1 Drawing Sheet

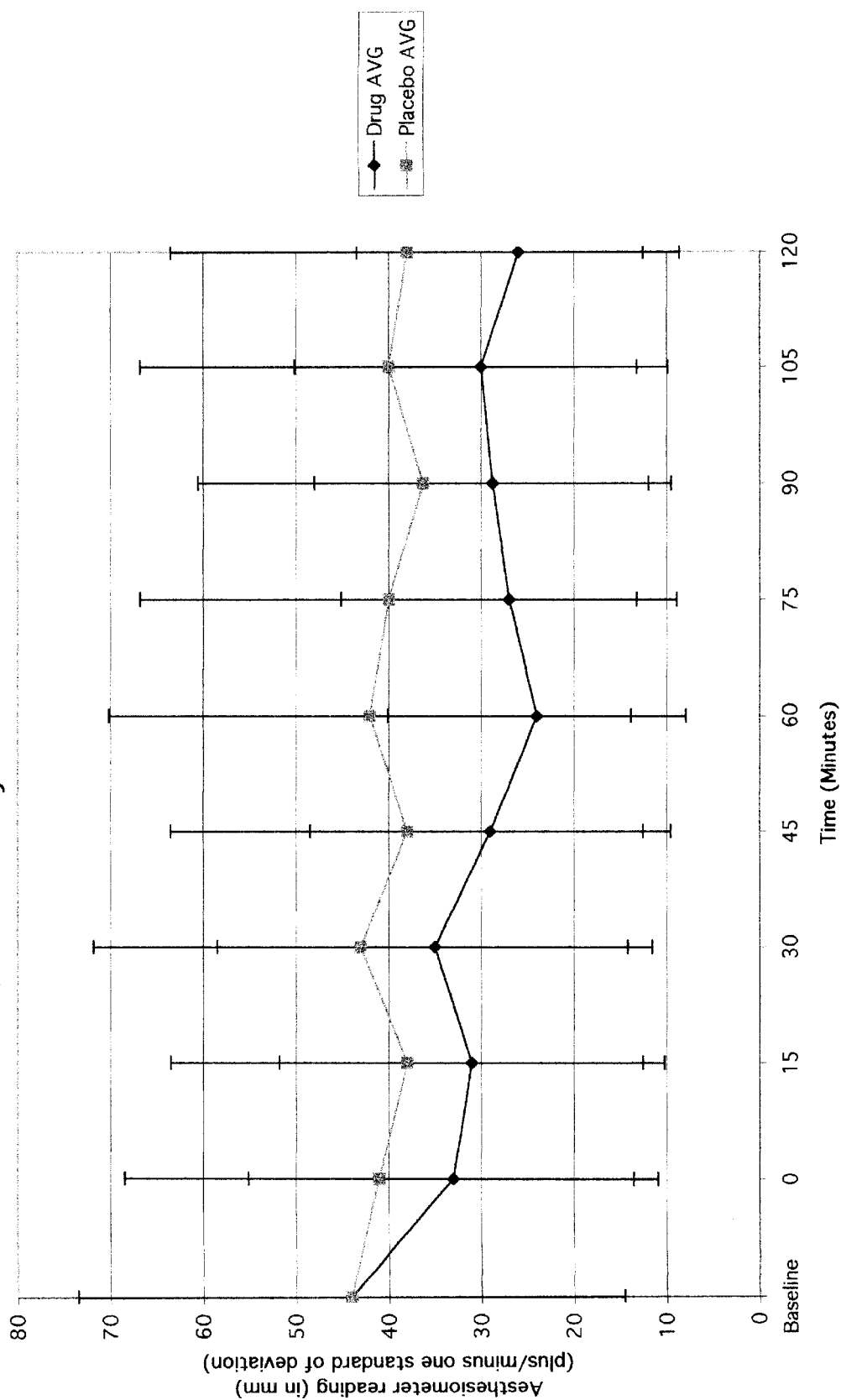

METHOD AND ANALGESIC PREPARATIONS FOR SUSTAINED AND EXTENDED CORNEAL ANALGESIA WITH SUBANESTHETIC CONCENTRATIONS OF LIDOCAINE

This is a continuation-in-part application of Ser. No. 09/442,066, filed Nov. 16, 1999, abandoned, which is a continuation of Ser. No. 09/088,594 filed Jun. 2, 1998, Abandoned, which is a continuation-in-part of Ser. No. 09/816,762, filed on Mar. 11, 1997, issued as U.S. Pat. No. 5,760,077 on Jun. 2, 1998 which is a continuation-in-part application of application Ser. No. 08/415,184 filed on Apr. 3, 1995, issued as U.S. Pat. No. 5,610,184 on Mar. 11, 1997 which is a continuation-in-part application of the application Ser. No. 08/183,186 filed on Jan. 14, 1994, Abandoned.

BACKGROUND OF THE INVENTION

1. Field of Invention

The current invention concerns a method for ophthalmic analgesia achieved with nontoxic subanesthetic concentration of multiple doses of topically administered lidocaine. In particular, the invention concerns administration of diluted topical lidocaine preparation comprising about and up to about 0.4% (4000 μg/ml) of lidocaine and a topical ophthalmic preparation for corneal analgesia having a fast onset of pain relief and extended duration of the corneal analgesia. The lidocaine preparation may be administered for several months without accompanying toxic symptoms.

2. Background Art and Related Art Disclosures

Trauma to the eye, particularly corneal injury and abrasion, tends to be excruciatingly painful. While many anesthetic agents such as proparacaine, cocaine, procaine, tetracaine, hexylcaine, bupivacaine, lidocaine, benoxinate, mepivacaine, prilocaine and etidocaine, to name a few, are well known to attain temporary anesthesia and suppression of pain, concentrations of these agents needed to achieve corneal anesthesia are between 0.25% and 4%. At these concentrations, these agents can only be administered for a very short period of time necessary to achieve local anesthesia and permit performance of ophthalmic procedures such as examination of a painful eye, measurement of intraocular pressure, gonioscopic examination, removal of foreign bodies and sutures from the cornea, diagnostic conjunctival and corneal scrapings, radial keratotomy, and other surgical procedures. The onset of the anesthesia is very rapid, typically under 15 seconds, and typically lasts for about 10–30 minutes.

Unfortunately, application of local anesthetics to the cornea at these concentrations causes the development of temporary superficial corneal epithelial lesions. Upon repeated application for prolonged anesthesia, these lesions progress to extensive erosions of the corneal epithelium and grayish infiltrates of the corneal stroma which can lead to permanent scarring and loss of vision. Prolonged application, of local anesthetics is further associated with delayed corneal reepithelialization after wounding, altered lacrimation and tear film stability, corneal swelling, and disruption of epithelial cell mitosis and migration.

It is therefore clear that the use of local anesthetics in their normal and intended manner is limited to short-term anesthesia and cannot be safely utilized for sustained decrease or elimination of pain over several hours or days.

Anesthesia, which is a partial or total loss of the sense of pain, temperature, and touch, is very different from analgesia, a state in which the individual does not feel pain but feels other sensations, such as touch or temperature.

Sustained ophthalmic analgesia is very difficult to achieve. This is particularly true with respect to corneal analgesia. The cornea is the clear dome-shaped window in the front of the eye. The cornea serves two functions. First, it forms the front part of the eye's outer wall and thus protects structures inside the eye. Second, with its curved shape, the cornea acts like a camera lens to transmit light and focus images on the retina at the back of the eye. The epithelium (outermost layer) of the cornea is heavily enervated. Therefore, the cornea is very sensitive, and any damage to the surface epithelium can cause severe pain.

A common cause of such pain is a break in the corneal epithelium. Such epithelial defects can be caused by corneal drying, infection and inflammation which damage epithelial cells, by corneal dystrophies with loosely adherent epithelium, or by mechanical removal of the corneal epithelium in traumatic abrasions or surgical procedures. In most cases, the pain persists until the epithelial defect has healed.

At present, in order to provide immediate but short-term alleviation of the severe pain experienced by patients suffering from corneal epithelial defects, commercially available local anesthetics can be applied topically to the eye, providing rapid onset of short-acting corneal anesthesia. Two commonly used topical anesthetics are proparacaine in a concentration of 0.5% (5,000 μg/ml) and tetracaine 0.5% (5,000 μg/ml). Lidocaine 4.0% (40,000 μg/ml) is also occasionally used.

While short-term relief from pain accompanies the application of these anesthetics, there are conditions of the cornea where such short term relief from pain is not sufficient and where prolonged analgesia is necessary and desirable. This is especially true for relief of pain associated with corneal epithelial defects. In these instances, the toxicity associated with repeated use of topical anesthetics for achieving sustained corneal analgesia has been well documented. In *Ocular Pharmacology,* Fifth Edition, CV Mosby, St. Louis, pages 75–76 (1983), the repeated use of anesthetic concentrations of topical anesthetics was found to be detrimental to the cornea, and the article states that the repeated use of anesthetics is prohibited because of their toxicity. Thus, the toxicity of these anesthetic agents precludes their repeated use for prolonged corneal analgesia. At this time, therefore, acceptable methods for long-term relief of corneal pain are limited to patching and oral analgesics.

Patching provides partial pain relief in some patients by reducing eyelid movement over the corneal surface and limiting exposure to the outside environment. However, patching has many disadvantages. It is difficult for the patient to reapply the patch properly when it becomes loose or soiled. Patching restricts the frequent use of topical medications. It raises the temperature of the eye surface and thus supports the growth of microorganisms. Finally, many patients are uncomfortable with an eye patched. While patching with a bandage soft contact lens may overcome some of these problems, patching provides incomplete pain relief in most patients and is no substitute for sustained analgesia in patients suffering from corneal epithelial defects, where the pain can persist for several days to several weeks or months.

Oral agents are reasonably effective in reducing corneal pain. However, onset of action is gradual and slow rather than immediate. Doses adequate for corneal analgesia are high and usually cause significant generalized sedation, occasionally accompanied by nausea and vomiting and rarely by life-threatening allergic reactions.

It would therefore be highly desirable and advantageous to have available a method for treatment of acute and chronic corneal pain without exposing a patient to the undesirable side effects of currently available oral analgesics, to the inadequate analgesia and inconvenience associated with patching, or to the toxic effects of repeated doses of currently available concentrations of topical anesthetics.

It is therefore the primary object of this invention to provide a method for achieving sustained and extended corneal analgesia by administration of analgesic concentrations of lidocaine formulated in topical ophthalmic analgesic solutions or ophthalmic analgesic preparations.

SUMMARY

One aspect of the current invention is a topical ophthalmic preparation for sustained corneal analgesia comprising diluted lidocaine.

Another aspect of the current invention is a topical ophthalmic preparation comprising diluted lidocaine for relief of corneal pain formulated as an ointment, cream, suspension, solution, gel or a sustained release vehicle comprising lidocaine of about and up to about 0.4%.

Still yet another aspect of the current invention is a method for safe alleviation of corneal pain by administration of an ophthalmic analgesic solution or preparation comprising diluted lidocaine administered on an as needed basis decided by the patient, as often and for as long as necessary.

DEFINITIONS

As used herein:

"Local anesthetics" means lidocaine.

"Dose" means a measurable amount of the ophthalmic analgesic for proper dosage containing from about and up to 0.4% of lidocaine.

"Microsystem" means a microdose or microdrop system wherein a topical lidocaine is present in concentrated form which is diluted by natural tearing process to subanesthetic concentrations not causing anesthesia.

"Microdose" or "microdrop" means a measurable amount of lidocaine present in one dose or one drop of a microsystem containing subanesthetic concentration from about and >0.4% of lidocaine in 1–10 µl of aqueous solution.

"Ophthalmic analgesic preparation" means any cream, gel, solution, sustained release vehicle or ointment containing lidocaine in a measurable dose, which preparation is suitable for topical ophthalmic use.

"Subanesthetic concentration" means concentration of lidocaine which produces an analgesic effect when applied topically to the cornea where analgesia is achieved without significant loss of corneal touch sensation and without anesthesia.

BRIEF DESCRIPTION OF FIGURES

FIG. 1 is a comparative graph of average corneal sensitivity in lidocaine treated eyes and in eyes treated with placebo.

DETAILED DESCRIPTION OF THE INVENTION

This invention concerns finding that diluted topical lidocaine of about and up to about 0.4% subanesthetic concentration achieves topical ophthalmic analgesia for sustained and extended corneal analgesia when applied topically to the cornea as a gel, cream, solution, sustained release vehicle or ointment preparation further optionally comprising pharmaceutically acceptable excipients, additives, or preservatives or other therapeutically effective agents.

The current invention concerns a topical pharmaceutical preparation suitable for administration of subanesthetic ultralow concentrations of lidocaine of about and up to 0.4%. Any and all concentrations of diluted lidocaine below 0.4% resulting in analgesia but not anesthesia are intended to be within the scope of the invention.

I. Analgesic Effect of Topical Lidocaine

Lidocaine administered topically in a typical manner at concentrations around 4.0% shows definite toxicity to the cornea and its use is therefore limited to short-term administration. Recently, experiments performed in vitro on rabbit cornea have indicated that low concentrations of lidocaine are not toxic to the cornea. The studies are described in *Investigative Ophthalmology and Visual Science*, 33:3029–3033 (1992). In this study, the endothelial or back surface of the cornea, not the epithelial surface, was perfused with various concentrations of lidocaine. Corneal toxicity, demonstrated as a delay in epithelial wound healing and corneal edema, was seen with endothelial perfusion concentrations >0.01% (100 µg/ml). Although this paper presents no data on analgesia, it cites a reference indicting that lidocaine 0.0005% (5.3 µg/ml) blocks tonic action potential discharges associated with corneal injury, again a rabbit cornea in vitro. They speculate that " . . . local anesthetics at analgesic concentrations of <100 µg/ml may be safe for continuous corneal administration and provide corneal analgesia after corneal abrasions or corneal refractive procedures. Further, in vivo clinical studies need to be conducted to establish the efficacy of such therapy before it is implemented."

It has now been surprisingly found that lidocaine preparations according to the invention provide extended and sustained analgesia to the injured or diseased human cornea in vivo in about and up to 0.4% (4000 µg/ml) concentration without causing corneal damage. This represents 40 times the maximum safe concentration described by the paper cited above. This analgesia is achieved without loss of corneal touch sensation, that is, without inducing corneal anesthesia.

The findings described herein have also demonstrated that concentrations of topical lidocaine as high as 0.4% (4000 µg/ml), or 800× the concentration described by the paper cited above as blocking action potentials in rabbit corneas in vitro, are still subanesthetic in human subjects.

The current results are neither obvious nor predictable from the prior disclosures. The main problem is the marked difference between rabbit and human models. An example of that difference is the finding described in *Am J. Opthalmol.*, 99:691 (1985) that proparacaine 0.05% (500 µg/ml) drops create anesthesia in the rabbit cornea, which was demonstrated not to be true in humans. In fact, other studies (*The Eye*, Vol. 1b, 109–110, Ed. H. Dawson, Academic Press (1984)) indicate that the rabbit cornea is about 50 times less sensitive than a human cornea. *Am. J. Opthalmol.*, (supra) also found that perfusing the rabbit cornea in vitro with proparacaine 0.3% (3000 µg/ml) for several days was not toxic to the epithelium, in marked contrast to the findings of *Investigative Ophthalmology and Visual Science*, 33:3029–3033 (1992). *Opthalmoligica*, 170:320 (1975) compared corneal anesthesia from soaps in rabbits and humans, found completely different responses, and concluded that "studies of corneal anesthesia in rabbits may not be extrapolated to the human eye." Thus, one skilled in the art would tend to discard speculation concerning human safety and efficacy based on a rabbit in vitro model, especially when patterns of use for topical anesthetics in humans are very firmly established.

The 0.4% lidocaine concentrations were found to achieve analgesia without any toxicity and without interference with healing, and are therefore both highly effective in relieving corneal pain and also safe for long term analgesia.

The preparation of the invention is formulated as a solution, suspension, gel, cream, ointment, or sustained release vehicle or using microsystem, such as microdrop or microdose systems. These microsystems involve extremely small volumes of the preparation to deliver >0.4% lidocaine, utilizing a natural propensity of the eye to dilute these small volumes with tears. The volumes used for this microsystem delivery are from about 1 to about 10 $\mu$l of the solution, suspension, gel, cream, ointment or sustained release vehicle.

The subanesthetic concentrations used in this invention were determined empirically, using drop volumes of approximately 30 $\mu$l. Since the volume of the normal tear film is approximately 7 $\mu$l, some dilution of any drop occurs when the drop is applied to the eye surface. Reflex tearing induced by drop application would, therefore, increase this dilution effect.

To determine whether the eye naturally dilutes the administered dosage of the therapeutic agent, lidocaine is administered in up to 10 times concentrated forms in microdrops or microvolumes of form about 1 to about 10 $\mu$l containing about and >0.4% of lidocaine. When these small microvolumes are used, then surface dilution due to a natural tearing becomes a significant factor in this delivery, and the higher concentrations of lidocaine achieve analgesia without anesthesia or toxicity.

The analgesic solution or preparation comprising lidocaine is administered to a patient suffering from corneal epithelial defect, whether of mechanical, inflammatory, infectious or chemical origin, caused by surgery, injury, diagnostic procedure or disease, as 1–3 volumes or an appropriate amount of sustained release vehicle, cream, ointment, gel or microsystem applied to the eye surface as needed for the relief of pain, such as every 5–30 minutes, every 1–6 hours, twice a day, or more or less frequently on an as needed basis, for as long as needed. A typical regimen is the administration of 1 drop of 0.4% solution every 15 minutes for 2 hours during the first day of the treatment followed by decreasing the number of applications as the epithelial defect heals and the pain subsides.

The patient uses a drop of the ophthalmic lidocaine solution or other lidocaine comprising ophthalmic preparation as often as necessary for the relief of pain. Therefore, the actual frequency of use is usually determined by the patient, and is dependent on the size and severity of the epithelial defect, the rate of healing, and the patient's pain threshold. In general, the ophthalmic lidocaine solution or preparation contains the lowest lidocaine concentration which consistently provides relief of pain for a patient or a population of patients, but this concentration may be increased up to 0.4%. Due to its safety, the analgesic solution or preparation of this invention can be used as frequently as necessary to control pain.

Ophthalmic analgesic solutions or preparations comprising lidocaine are safe for repeated topical administration to the eye as often as necessary for as long as several months.

The frequency of the administration to achieve subanesthetic analgesia but not anesthesia depends on the type of the anesthetic, on the concentration of the anesthetic, and on the formulation of the anesthetic. The determination of such regimen is within the artisans skills. Any regimen of any topical ophthalmic anesthetic achieving subanesthetic analgesia without anesthesia, regardless of the drug, its concentration or formulation is intended to be within the scope of the invention.

The current finding is that lidocaine can be safely administered up to about 0.4% without causing anesthesia, and that at this concentration it is non-toxic to the cornea while providing good and long lasting analgesia. The results were surprising and unexpected in view of the above prior findings.

Previous studies have demonstrated that single and multiple doses of 0.05% topical proparacaine are subanesthetic, that is, they do not cause the loss of corneal touch sensation.

The current studies for determination of subanesthetic concentrations of multiple doses of topical lidocaine were performed on twelve subjects. Various dilutions of topical lidocaine were instilled every 15 minutes for 2 hours in one eye, the fellow eye receiving placebo drops in a double masked fashion. Corneal sensation was tested every 15 minutes. Aesthesiometer data is shown in Tables 1–4. The maximum subanesthetic concentration of topical lidocaine was found to be approximately 0.4% (4000 $\mu$g/ml), compared to the maximum subanesthetic concentration for topical proparacaine, tetracaine, and bupivacaine, which were found to be approximately 0.05% (500 $\mu$g/ml). Therefore, lidocaine appears to be subanesthetic at a concentration approximately 8× higher than that of these other anesthetics.

TABLE 1

Drug: Lidocaine 0.1%

| Time (min.) | Patient 1 Drug | Placebo |
|---|---|---|
| Baseline | 40 | 40 |
| 0 | 15 | 40 |
| 15 | 20 | 25 |
| 30 | 15 | 40 |
| 45 | 20 | 30 |
| 60 | 10 | 35 |
| 75 | 15 | 40 |
| 90 | 15 | 30 |
| 105 | 20 | 35 |
| 120 | 20 | 30 |

Table 1 shows corneal aesthesiometer readings as a measure of corneal sensation. Lower values indicate less corneal sensation. After applying lidocaine 0.1% for 2 hours, corneal sensation is decreased but still present.

TABLE 2

Drug: Lidocaine 0.2%

| | Patient 1 | | Patient 2 | | Patient 3 | | Patient 4 | |
|---|---|---|---|---|---|---|---|---|
| Time (min.) | Drug | Placebo | Drug | Placebo | Drug | Placebo | Drug | Placebo |
| Baseline | 50 | 50 | 40 | 50 | 50 | 50 | 40 | 40 |
| 0 | 25 | 30 | 40 | 30 | 30 | 45 | 30 | 30 |
| 15 | 30 | 30 | 20 | 50 | 30 | 30 | 20 | 30 |
| 30 | 10 | 20 | 40 | 50 | 30 | 25 | 20 | 30 |
| 45 | 15 | 30 | 30 | 40 | 20 | 30 | 30 | 50 |

TABLE 2-continued

Drug: Lidocaine 0.2%

| | Patient 1 | | Patient 2 | | Patient 3 | | Patient 4 | |
|---|---|---|---|---|---|---|---|---|
| Time (min.) | Drug | Placebo | Drug | Placebo | Drug | Placebo | Drug | Placebo |
| 60 | 25 | 40 | 20 | 40 | 20 | 30 | 20 | 30 |
| 75 | 15 | 30 | 20 | 40 | 15 | 30 | 20 | 30 |
| 90 | 25 | 40 | 20 | 30 | 20 | 35 | 15 | 40 |
| 105 | 20 | 40 | 20 | 40 | 20 | 35 | 20 | 30 |
| 120 | 20 | 30 | 20 | 40 | 15 | 40 | 20 | 30 |

Table 2 shows corneal aesthesiometer readings as a measure of corneal sensation. Lower values indicate less corneal sensation. After applying Lidocaine 0.2% for 2 hours, corneal sensation is decreased but still present.

TABLE 3

Drug: Lidocaine 0.4%

| | Patient 1 | | Patient 2 | | Patient 3 | | Patient 4 | | Patient 5 | |
|---|---|---|---|---|---|---|---|---|---|---|
| Time (min.) | Drug | Placebo | Drug | Placebo | Drug | Placebo | Drug | Placebo | Drug | Placebo |
| Baseline | 35 | 40 | 45 | 40 | 40 | 40 | 40 | 40 | 60 | 60 |
| 0 | 20 | 35 | 30 | 40 | 25 | 30 | 30 | 40 | 60 | 60 |
| 15 | 15 | 30 | 25 | 30 | 25 | 30 | 40 | 50 | 50 | 50 |
| 30 | 20 | 35 | 25 | 30 | 45 | 50 | 25 | 40 | 60 | 60 |
| 45 | 15 | 35 | 25 | 25 | 30 | 30 | 25 | 40 | 50 | 60 |
| 60 | 20 | 40 | 20 | 30 | 20 | 30 | 20 | 50 | 40 | 60 |
| 75 | 25 | 40 | 20 | 30 | 15 | 35 | 25 | 35 | 50 | 60 |
| 90 | 30 | 30 | 20 | 25 | | | 15 | 30 | 50 | 60 |
| 105 | 30 | 30 | 15 | 30 | 20 | 30 | 25 | 50 | 60 | 60 |
| 120 | 25 | 35 | 10 | 30 | 15 | 30 | 20 | 35 | 60 | 60 |

Table 3 shows central aesthesiometer readings as a measure of corneal sensation. Lower values indicate less corneal sensation. Lidocaine 0.4% does not eliminate corneal sensation.

TABLE 4

Drug: Lidocaine 1.0%

| | Patient 1 | | Patient 2 | |
|---|---|---|---|---|
| Time (min.) | Drug | Placebo | Drug | Placebo |
| Baseline | 50 | 50 | 50 | 50 |
| 0 | 20 | 50 | 40 | 50 |
| 15 | 20 | 50 | 30 | 50 |
| 30 | 15 | 50 | 20 | 50 |
| 45 | 20 | 40 | 10 | 50 |
| 60 | 20 | 40 | 10 | 40 |
| 75 | 15 | 50 | 10 | 50 |
| 90 | 20 | 50 | 10 | 50 |
| 105 | 10 | 35 | 10 | 40 |
| 120 | 15 | 35 | 10 | 35 |
| 125 | (2.0%) 5 | (2.0%) 0 | (2.0%) 5 | (2.0%) 5 |

Table 4 shows central aesthesiometer readings as a measure of corneal sensation. Lower values indicate less corneal sensation, with values of 0–10 mm approximating no corneal sensation. Lidocaine 1.0–2.0% eliminates corneal sensation.

The results of these studies are seen in FIG. 1. FIG. 1 is a comparative graph illustrating an average corneal sensitivity, as determined by 0.12 mm aesthesiometer reading in mm, after multiple doses of 0.4% lidocaine. Drops were instilled in 15 minute intervals for two hours. The fellow eye of each patient was treated with placebo. As seen in Table 3 and FIG. 1, although there appears to be some decrease in corneal sensation when 0.4% lidocaine was applied using this system, no significant difference between the treatment and placebo groups could be demonstrated. At no time was corneal anesthesia induced. Therefore, multiple doses of 0.4% topical lidocaine are subanesthetic.

In absolute amounts, the active ingredient, that is, lidocaine, is administered in amounts from about 0.30 μg to about 120 μg/per one dose. The dose is calculated as follows. The 0.005% analgesic solution contains 50 μg of local anesthetic per 1 ml of solution. One drop of the commercial ophthalmic solution typically ranges from 30–70 μl, however, since the maximum volume of the cul-de-sac is only 30 μl, only 30 μl of the solution is delivered to the cornea. In 1 ml of the 0.005% solution (50 μg/ml), there are approximately 33 drops. In each drop, therefore, there is about 1.5 μg/drop of anesthetic actually delivered to the cornea. In less concentrated solutions of 0.0025% and 0.001%, the absolute amount of anesthetic delivered to the cornea per one drop of the analgesic solution is about 0.75 μg and 0.30 μg respectively. The concentration of the anesthetic in other ophthalmic analgesic preparations is generally equivalent to that in the ophthalmic analgesic solutions, and the amount of anesthetic administered via the ointment, cream, gel or sustained release vehicle will be generally be similar to that delivered by the solution.

In its broadest aspect, the invention concerns a method for alleviating corneal pain by administration of ophthalmic analgesic solutions or preparations comprising lidocaine in a specified range of concentrations, such solutions or preparations to be applied topically in effective doses to the human cornea in vivo to safely provide sustained analgesia when corneal epithelial defects are present.

Evaluation of the toxicity of diluted topical lidocaine was performed on two subjects and the safety of the current method and current preparations are demonstrated. Two subjects were enrolled in this study. Lidocaine 0.4% drops were instilled every 15 minutes for 10 hours in one eye, the fellow eye receiving placebo drops in a double masked fashion. Visual acuity, slit lamp examination of the cornea, corneal sensation, and corneal thickness were unchanged in either eye. In conclusion, no adverse effects of the drug were seen in either subject. Repeated doses had no detrimental effect on the cornea.

At anesthetic concentrations, lidocaine is known to cause complete nerve depolarization and to block all transmission. In agreement with this observation, higher doses than 0.4% lidocaine depolarized the nerve, blocked all nerve transmission and eliminated corneal sensation.

At subanesthetic concentrations of the topical lidocaine, the nerve was not depolarized, nerve transmission was present and corneal sensation remained. Thus, topical lidocaine administered in subanesthetic concentrations substantially decreased or eliminated the pain but did not eliminate corneal sensation. Consequently, since the cornea was still sensitive to touch, lidocaine did not depolarize the nerve, as observed following the anesthesia, but it provides true analgesia which was physiologically determinable and distinguishable from anesthesia.

Topical Ophthalmic Preparations

In practice of the current invention, the ophthalmic lidocaine solution is prepared by diluting commercially available lidocaine. Lidocaine is topically formulated in about 10 to 500 times diluted form as gel, cream, sustained release vehicle or ointment.

These physiologically compatible preparations can be made of or additionally contain any pharmaceutically acceptable excipient, additive or preservative such as for example sodium chloride, potassium chloride, benzalkonium chloride, boric acid, sodium borate, sodium bicarbonate, sodium sulfite, sodium acid phosphate, disodium phosphate, disodium edetate, disodium sulfate, sodium citrate, calcium chloride, sodium lactate, magnesium chloride, polyethylene glycol 300 and 400, povidone, carboxymethylcellulose, hydroxypropylmethylcellulose, glycerin, polyvinyl alcohol, Dextran 70, dextrose, polyquaterium 1, thimerosal, phenylmercuric nitrate, chlorbutanol, sorbic acid, hydrochloric acid or sodium hydroxide to adjust the pH, and other ophthalmologically acceptable agents added in concentrations which are non-toxic to the cornea. The local anesthetics and the pharmaceutically acceptable excipients, additives or preservatives are dissolved in sterile distilled or sterile purified water to provide a solution physiologically compatible with the eye. The final concentration of lidocaine in these new ophthalmic analgesic solutions is thus from about 0.001% to about 0.4%.

Additionally, these topical ophthalmic preparations are advantageously formulated in combination with other drugs, such as other topical anesthetics in ultralow concentrations, analgesics, antiinflamatories, antibiotics, astringents, antiseptics, etc., and such other therapeutic agents which are typically used in topical ophthalmic preparations.

The ophthalmic lidocaine preparation in the form of a cream, gel, solution, suspension, ointment, or a sustained release vehicle typically delivers from about 0.001% to about 0.4% local anesthetic per dose.

The above agrees with previous observations that under normal conditions, the human tear volume averages about 71 $\mu$l. The estimated maximum volume of the eye cul-de-sac is about 30 $\mu$l with drainage capacity far exceeding lacrimation rate. The outflow capacity accommodates the sudden large volume resulting from the instillation of an eye drop or from the administration of other preparations. Most commercial eye drops range from 30 to 75 $\mu$l in volume. However, much in excess of 30 $\mu$l is unable to enter the cul-de-sac and is removed by drainage. The Microsystems of the invention utilizes natural tearing to provide the dilution of the concentrated anesthetics into the analgesic concentrations.

Typically, in the practice of the current invention, one volume of an ophthalmic lidocaine solution consisting essentially of about and up to 0.4% of a lidocaine as listed above, formulated in any pharmaceutically acceptable excipient physiologically compatible with the eye surface, or formulated in other pharmaceutically acceptable vehicles and preparations, is administered repeatedly to a patient's cornea for sustained and extended pain relief.

Ophthalmic preparations of the invention, as described above, are also advantageously prepared according to *Remington's Pharmaceutical Sciences,* Chapters 87 and 92, pages 1553–1566 and 1644–1661, 17th Edition (1985) or any subsequent edition, Eds. Gennaro, R. A., et al.

Typically, suspensions and solutions are aqueous, ointments and creams typically contain a white petrolatum-mineral oil base. Typically, they are formulated as multidose products but may be also, for convenience, be formulated as a single dose product. The preparations are sterile and stabilized.

Ophthalmic suspensions of the invention are dispersions of a finely divided drug substances in an aqueous vehicle containing suitable suspending and dispersing agents as well as a suspended lidocaine in subanesthetic concentrations from about and up to about 0.4%.

Ophthalmic concentrated suspension, such as, for example, a concentrated suspension of lidocaine is especially suitable for micro-system preparations where the concentration of the drug is from about 0.01% to >4.0% per 1–10 $\mu$l.

Ophthalmic solutions of the invention are aqueous preparations of lidocaine of the invention dissolved in an appropriate aqueous solvent, typically artificial tears, saline or distilled water in concentration from about 0.001%–0.4% per drop to be used directly.

Ophthalmic gels of the invention are preparations containing high-molecular weight polymers, additives and preservatives with adjusted pH and osmolarity to ophthalmologically acceptable levels. High molecular weight polymers are either synthetic, such as carbomer 940 (polyacrylic acid) or natural, such as hyaluronic acid or alginates. Lidocaine is formulated to contain a subanesthetic concentration of the anesthetic per one dosage volume, such dosage preferably containing from about and up to about 0.4% of lidocaine. Ophthalmic ointments or creams of the invention contain the drug fully dispensed in an ointment or cream base. In addition to the drug content being from about and up to about 0.4% per one dosage volume, these ointments typically contain antimicrobial agents such as chlorobutanol, parabens, substituted alcohols and phenols, or one of the organic mercurials. Care is taken that the ointment or cream does not contain particulate matter.

In addition, the agents of the invention may be formulated in sustained-release vehicles where lidocaine is formulated such that it is released within a certain period of time such as 12 hours or longer. The sustained-release vehicles may advantageously utilize reservoirs such as for example a commercially available Ocusert implant available from Akorn, which can deliver the drug of the invention for up to 1 week. Other delivery vehicles, such as, for example, the colloidal drug delivery systems, microcapsules, nanocapsules, macromolecular complexes, polymeric spheres, microspheres or liposomes are also intended to be within the scope of the invention as long as they are non-toxic and non-irritating to the eye.

Typically, the ophthalmic formations of the invention will contain some or all of the pharmaceutically acceptable ophthalmic excipients, preservative or, additives named above, appropriate for preparation of the formulations for the invention. These excipients and additives are present in concentrations known and used in the art for ophthalmic formulations in concentrations acceptable in pharmaceutical sciences.

Ophthalmic preparations typically have neutral or slightly acidic pH between about pH 5 and 7.5 and are optionally buffered to maintain the proper pH throughout the extent of product shelf life. However, any other pH at which the ophthalmic preparation of the invention may be safely administered is within the scope of the invention.

Utility

The ophthalmic lidocaine preparations and the method of treatment described herein are useful for alleviation of pain of the eye caused by corneal epithelial defects secondary to trauma, drying, infection, inflammation, surgery, corneal dystrophy, or other cause. The method is fast and safe and immediately causes substantial or complete relief of pain. The analgesic solution or preparation contains lidocaine in about and up to 0.4% and by repeated applications or continuous release safely provides sustained and extended topical analgesic effect on the cornea. The solution is easily prepared in a sterile form, has practical shelf-life and is easy to administer.

EXAMPLE 1

Determination of Subanesthetic Properties of Multiple Doses of Dilute Topical Lidocaine This example describes clinical evaluation of various dilutions of lidocaine administered to twelve volunteer subjects as a topical 0.1%, 0.2%, 0.4% and 1% solution.

Following informed consent, twelve subjects were each provided with a solution of eye drops containing 0.1% (one subject), 0.2% (four subjects), 0.4% (five subjects) and 1% (two subjects) of lidocaine. The solution was administered in comparative manner where one drop of the solution was instilled into one eye and the placebo was instilled into the fellow eye in a double-masked fashion. Corneal aesthesiometer readings were taken at baseline and zero, 15, 30, 45, 60, 75, 90, 105 and 120 minutes.

Results are seen in Tables 1–4 and FIG. 1.

EXAMPLE 2

Clinical Evaluation of Analgesic Effects and Safety of 0.4% Lidocaine

This example describes clinical evaluation of pain relief obtained with administration of 0.4% lidocaine topical solution.

Following informed consent, nine patients were each given a bottle of eye drops consisting of 0.4% lidocaine solution. They were instructed to use a drop as often as every 15 minutes as needed for pain relief following laser vision correction surgery (photorefractive keratectomy). Seven of the nine patients reported that the lidocaine drops were helpful in relieving their postoperative pain. There was no delay in epithelial healing in all nine treated patients.

EXAMPLE 3

Microsystem Delivery of the Topical Analgesic Preparation

This example describes an alternative preparation utilizing microsystem delivery of the topical ophthalmic analgesic preparations. The microsystem utilizes either microdrop or microdose delivery and the natural propensity of the eye to tear and in this way to dilute the higher concentration of the anesthetic into the analgesic concentration.

The subanesthetic concentrations used in this invention are determined empirically, using drop volumes of approximately 30 $\mu$l. Since the volume of the normal tear film is approximately 7 $\mu$l, some dilution of any drop occurs when the drop is applied to the eye surface. Reflex tearing induced by micro drop application increases this dilution effect.

When smaller drop volumes are used, in microdrops from about 1 to about 10 $\mu$l, then surface dilution becomes a significant factor, and higher concentrations of anesthetic are used to achieve analgesia without anesthesia or toxicity.

For this study, 1.0 $\mu$l of 1.0–4.0% of the topical anesthetic is applied to the eye surface and the dilution is observed. A rapid dilution, to subanesthetic concentration, occurs considering tear film volume and reflex tearing. Thus, in this case, the resulting drug concentration on the eye surface is such that it provides analgesia but is not anesthetic.

This alternative method for achieving non-anesthetic and nontoxic concentrations on the eye surface uses significantly smaller volumes of higher concentrations (>0.4%) of anesthetic solution.

What is claimed is:

1. A topical ophthalmic analgesic preparation comprising about and up to 0.4% lidocaine said preparation further containing pharmaceutically acceptable excipients, additives or preservatives.

2. The preparation of claim 1 formulated as an ointment, cream, suspension, solution, gel or a sustained release vehicle wherein the subanesthetic concentration is from about 0.001% to about 0.4%.

3. The preparation of claim 2 formulated as the ointment.

4. The preparation of claim 2 formulated as the cream.

5. The preparation of claim 2 formulated as the gel.

6. The preparation of claim 2 formulated as the sustained release vehicle.

7. An ophthalmic analgesic microdose preparation consisting essentially of from about 0.01% to about 4% of lidocaine diluted in about 1 to about 10 $\mu$l of aqueous solution comprising pharmaceutically acceptable excipients, additives or preservatives, said preparation administered topically to the eye in about 1 to about 10 $\mu$l dosage.

8. The preparation of claim 7 formulated as an ointment.

9. The preparation of claim 7 formulated as a solution.

10. The preparation of claim 7 formulated as a gel.

11. The preparation of claim 7 formulated as a sustained release vehicle.

12. A method for topical ophthalmic analgesia comprising a step of administering to a subject in need thereof, an ophthalmic preparation comprising about and up to 0.4% lidocaine.

13. The method of claim 12 wherein the preparation is an ointment, cream, suspension, solution, gel or sustained release vehicle.

14. The method of claim 13 wherein the preparation is the solution.

15. The method of claim 13 wherein the preparation is the ointment.

16. The method of claim 13 wherein the preparation is the cream.

17. The method of claim 13 wherein the preparation is the gel.

18. The method of claim 13 wherein the preparation is the sustained release vehicle.

19. The preparation of claim 7 wherein 4% lidocaine is diluted in about 10 $\mu$l of aqueous solution.

20. The preparation of claim 12 administered in 10 $\mu$l dosage.

* * * * *

UNITED STATES PATENT AND TRADEMARK OFFICE
CERTIFICATE OF CORRECTION

PATENT NO.    : 6,350,781 B1
DATED         : February 26, 2002
INVENTOR(S)   : Lee Shahinian, Jr.

It is certified that error appears in the above-identified patent and that said Letters Patent is hereby corrected as shown below:

<u>Title page,</u>
Under United States Patent delete "SHAHINIA" and replace with -- SHAHINIAN --;
Item [76], Inventor, delete "SHAHINIA" and replace with -- SHAHINIAN --.

Signed and Sealed this

Twenty-third Day of April, 2002

*Attest:*

JAMES E. ROGAN
*Attesting Officer*          *Director of the United States Patent and Trademark Office*